(12) United States Patent
Rokde et al.

(10) Patent No.: US 10,357,389 B2
(45) Date of Patent: *Jul. 23, 2019

(54) GASTRIC TUBES HAVING TETHERED PLUGS AND METHODS OF USE

(71) Applicant: Covidien LP, Mansfield, MA (US)

(72) Inventors: Rajat Rokde, Pune (IN); Syed Ahmed Mushtaque, Andhra Pradesh (IN); Jeetendra Bharadwaj, Andhra Pradesh (IN)

(73) Assignee: Coviden LP, Mansfield, MA (US)

( * ) Notice: Subject to any disclaimer, the term of this patent is extended or adjusted under 35 U.S.C. 154(b) by 322 days.

This patent is subject to a terminal disclaimer.

(21) Appl. No.: 15/233,093

(22) Filed: Aug. 10, 2016

(65) Prior Publication Data

US 2016/0346110 A1 Dec. 1, 2016

Related U.S. Application Data

(63) Continuation of application No. 14/276,303, filed on May 13, 2014, now Pat. No. 9,414,947.

(51) Int. Cl.
*A61F 5/00* (2006.01)
*A61M 1/00* (2006.01)
(Continued)

(52) U.S. Cl.
CPC ............ *A61F 5/0073* (2013.01); *A61B 17/22* (2013.01); *A61B 90/06* (2016.02); *A61F 5/0076* (2013.01);
(Continued)

(58) Field of Classification Search
CPC ...... A61F 2200/0058; A61F 2200/0075; A61F 2200/0068; A61F 2/02; A61F 2/07;
(Continued)

(56) References Cited

U.S. PATENT DOCUMENTS 3,227,154 A 1/1966 Cook
4,328,805 A 5/1982 Akopov et al.
(Continued)

FOREIGN PATENT DOCUMENTS

CN 201365906 Y 12/2009
CN 102626536 A 8/2012
(Continued)

OTHER PUBLICATIONS

European Communication, dated May 26, 2017, corresponding to European Application No. 15167342.3; 4 pages.
(Continued)

*Primary Examiner* — Leslie R Deak

(57) ABSTRACT

A gastric tube for use in a bariatric procedure includes an elongate tube and a cannulated plug coupled to the elongate tube. The elongate tube has a proximal end portion and a distal end portion. The elongate tube defines a lumen along a length thereof. The proximal end portion defines an opening in communication with the lumen. The elongate tube includes a blunt tip and an outer surface. The blunt tip is formed on the distal end portion. The outer surface defines a side opening in communication with the lumen. The cannulated plug includes a proximal end and a distal end. The proximal end is configured for connection to a vacuum source. The distal end is configured for removable receipt in the opening of the proximal end portion of the elongate tube to control a flow of one of aspiration and irrigation through the lumen.

20 Claims, 6 Drawing Sheets

(51) Int. Cl.
*A61M 3/02* (2006.01)
*A61M 25/00* (2006.01)
*A61M 39/22* (2006.01)
*A61B 17/22* (2006.01)
*A61B 90/00* (2016.01)
*A61B 17/00* (2006.01)

(52) U.S. Cl.
CPC .......... *A61F 5/0083* (2013.01); *A61F 5/0089* (2013.01); *A61M 1/0062* (2013.01); *A61M 1/0084* (2013.01); *A61M 3/0279* (2013.01); *A61M 25/007* (2013.01); *A61M 39/22* (2013.01); *A61B 2017/00818* (2013.01); *A61B 2017/22062* (2013.01); *A61B 2017/22079* (2013.01); *A61B 2090/061* (2016.02)

(58) Field of Classification Search
CPC .... A61F 2/90; A61F 2/91; A61F 2/915; A61F 5/005; A61F 5/056; A61F 5/0076; A61F 5/0083; A61F 5/0089
See application file for complete search history.

(56) References Cited

U.S. PATENT DOCUMENTS

| | | | |
|---|---|---|---|
| 5,297,536 | A | 3/1994 | Wilk |
| 5,382,231 | A | 1/1995 | Shlain |
| 5,401,241 | A | 3/1995 | Delany |
| 5,458,131 | A | 10/1995 | Wilk |
| 5,465,709 | A | 11/1995 | Dickie et al. |
| 5,718,666 | A | 2/1998 | Alarcon |
| 7,153,131 | B2 | 12/2006 | Crohn |
| 8,092,378 | B2 | 1/2012 | Roth et al. |
| 8,147,502 | B2 | 4/2012 | Albrecht et al. |
| 8,192,448 | B2 | 6/2012 | Bessler et al. |
| 8,454,503 | B2 | 6/2013 | Roth et al. |
| 8,663,149 | B2 | 3/2014 | Gagner et al. |
| 9,414,947 | B2 * | 8/2016 | Rokde .................. A61F 5/0076 |
| 2004/0006351 | A1 | 1/2004 | Gannoe et al. |
| 2004/0092974 | A1 | 5/2004 | Gannoe et al. |
| 2005/0119674 | A1 | 6/2005 | Gingras |
| 2005/0203489 | A1 | 9/2005 | Saadat et al. |
| 2005/0251158 | A1 | 11/2005 | Saadat et al. |
| 2006/0200004 | A1 | 9/2006 | Wilk |
| 2006/0241344 | A1 | 10/2006 | Wilk |
| 2006/0241570 | A1 | 10/2006 | Wilk |
| 2007/0032702 | A1 | 2/2007 | Ortiz |
| 2010/0179417 | A1 | 7/2010 | Russo |
| 2011/0178454 | A1 | 7/2011 | Gagner et al. |
| 2011/0288576 | A1 | 11/2011 | Hoffman |
| 2012/0065469 | A1 | 3/2012 | Allyn et al. |
| 2012/0165608 | A1 | 6/2012 | Banik et al. |
| 2012/0184981 | A1 | 7/2012 | Pecor et al. |
| 2012/0239061 | A1 | 9/2012 | Mathur |
| 2013/0165774 | A1 * | 6/2013 | Nocca .................. A61F 5/0083 600/431 |
| 2014/0018722 | A1 | 1/2014 | Scott et al. |
| 2014/0114121 | A1 | 4/2014 | Trivedi |

FOREIGN PATENT DOCUMENTS

| | | |
|---|---|---|
| ES | 2326937 A1 | 10/2009 |
| JP | 3178309 B2 | 6/2001 |
| WO | 02096327 A2 | 12/2002 |
| WO | 2009097585 A1 | 8/2009 |
| WO | 2012138737 A1 | 10/2012 |
| WO | 2013123235 A1 | 8/2013 |
| WO | 2014062881 A1 | 4/2014 |

OTHER PUBLICATIONS

European Search Report dated Mar. 24, 2017, corresponding to European Application No. 16199748.1; 5 pages.
Extended European Search Report dated Oct. 1, 2015, corresponding to European Application No. 15167342.3; 7 pages.
Dietel et al., "Endoscopy of Vertical Banded Gastroplasty," The American Surgeon, May 1989, vol. 55; pp. 287-890.
Dietel et al., "Vertical Banded Gastroplasty: Results in 233 Patients," The Canadian Journal of Surgery, Sep. 1986, vol. 29, No. 5; pp. 322-324.
Mason et al., "Vertical Gastroplasty: Evolution of Vertical Banded Gastroplasty,"World Journal of Surgery, Sep. 1998, vol. 22, No. 9; pp. 919-924.
European Search Report, dated Mar. 19, 2015, corresponding to European Application No. 14192226.0; 7 pages.
European Search Report, dated Mar. 24, 2015, corresponding to European Application No. 14192416.7; 7 pages.
Extended European Search Report dated Sep. 17, 2015, corresponding to European Patent Application 15167339.9; 10 pages.
European Search Report dated Dec. 2, 2015, corresponding to European Application No. 151772332; 7 pages.

* cited by examiner

GASTRIC TUBES HAVING TETHERED PLUGS AND METHODS OF USE

CROSS-REFERENCE TO RELATED APPLICATIONS

This application is a continuation application of U.S. patent application Ser. No. 14/276,303 filed on May 13, 2014, the entire contents of which is incorporated by reference herein.

TECHNICAL FIELD

The present disclosure generally relates to surgical instruments, and more particularly, to a gastric tube having a tethered plug used in bariatric procedures.

BACKGROUND

Obesity is reaching epidemic proportions in many regions of the world, particularly in the United States. In order to treat obesity, various bariatric procedures have been developed including, for example, gastric bypass, adjustable gastric banding, and sleeve gastrectomy. The goal in each of these procedures is to reduce the stomach capacity to restrict the amount of food that the patient can eat. The reduced stomach capacity, in turn, results in a feeling of fullness for the patient after ingesting a relatively smaller amount of food. Thus, the patient can achieve significant weight loss.

Sleeve gastrectomy involves transecting a stomach, e.g., using a stapling device or other suitable device, to reduce a stomach volume. Sleeve gastrectomy procedures are often aided by the use of a gastric tube, which serves as a guide or template for transecting the stomach to the appropriate configuration while inhibiting inadvertent transection of stomach or esophageal tissue. Once the stomach has been appropriately transected, the gastric tube is removed and a leak test is performed to determine whether there are any areas of extravasation.

In use, the gastric tube may be advanced into a patient's body through an oral cavity and down through the esophagus into the stomach to provide delineation of the antrum of the stomach, irrigation/suction of fluids, and/or a sizing of a gastric pouch. While being advanced, due at least in part to the circuitous nature of this track, a clinician may need to reposition the gastric tube in various orientations until the gastric tube is properly aligned or bypasses any obstruction(s).

Accordingly, a more flexible gastric tube would aid a clinician in navigating the gastric tube through body cavities of a patient. Further, a more efficient way of connecting and disconnecting a vacuum source with the gastric tube would avoid vacuum pressure loss and/or spillage of bodily fluid.

SUMMARY

According to one aspect of the present disclosure, a gastric tube for use in a bariatric surgical procedure is provided. The gastric tube includes an elongate tube and a cannulated plug attached to the elongate tube. The elongate tube has a proximal end portion and a distal end portion. The elongate tube defines a lumen along a length thereof. The proximal end portion defines an opening in communication with the lumen. The elongate tube includes a blunt tip and an outer surface. The blunt tip is formed on the distal end portion. The outer surface extends between the proximal and distal end portions and defines a side opening in communication with the lumen. The side opening is configured and dimensioned for at least one of aspiration and irrigation.

The cannulated plug includes a proximal end and a distal end. The proximal end is configured for connection to a vacuum source. The distal end is configured for removable receipt in the opening of the proximal end portion of the elongate tube to control a flow of one of aspiration and irrigation through the lumen.

In embodiments, the plug may include a tether attached to the outer surface of the elongate tube. In further embodiments, the plug may include a radial extension and the elongate tube may include an inner surface. The radial extension may have an outer diameter equal to a diameter of the opening of the proximal end portion such that the radial extension is frictionally engaged with the inner surface of the elongate tube when the plug is received in the opening. In some embodiments, the plug may taper between the proximal end and the distal end thereof. The distal end of the plug may include a plurality of stacked conical bodies. It is contemplated that the plug may include a valve resiliently biased towards a closed position.

In some aspects of the present disclosure, the elongate tube may be pliable. In embodiments, the tip of the elongate tube may have an arcuate outer surface. The elongate tube may further include a recess formed in the tip configured for at least one of aspiration and irrigation. The elongate tube may further include a plurality of depth markings formed along at least a portion of the outer surface.

In embodiments, the gastric tube may further include a balloon supported on the elongate tube configured to receive an inflation medium to inflate the balloon.

In embodiments, the gastric tube may further include a movable component attached to the outer surface. The movable component may be movable between an unexpanded position in which the movable component is disposed in abutting engagement with the outer surface and an expanded position in which a distal portion of the movable component bows outwardly from the outer surface of the elongate tube. The movable component may be slidably coupled to the proximal end portion of the elongate tube and fixedly coupled to the distal end portion of the elongate tube.

According to another aspect of the present disclosure, a method of performing a bariatric procedure is provided. The method includes providing a gastric tube including an elongate tube and a cannulated plug coupled to the elongate tube. The elongate tube has a proximal end portion and a distal end portion. The elongate tube defines a lumen along a length thereof. The proximal end portion defines an opening in communication with the lumen. The elongate tube includes a blunt tip and an outer surface. The blunt tip is formed on the distal end portion. The outer surface extends between the proximal and distal end portions and defines a side opening in communication with the lumen. The side opening is configured and dimensioned for at least one of aspiration and irrigation The cannulated plug includes a proximal end and a distal end. The proximal end is configured for connection to a vacuum source. The distal end is configured for removable receipt in the opening of the proximal end portion of the elongate tube to control a flow of one of aspiration and irrigation through the lumen.

The method further includes inserting the gastric tube into an oral cavity of a patient; guiding the gastric tube along an enteral pathway; repositioning the gastric tube based on an observed position of the tip to a selected position within a stomach of the patient; aspirating fluid from the stomach through the side opening of the elongate tube; anchoring the gastric tube to the selected position within the stomach; and transecting a portion of the stomach.

In embodiments, the method may further include removing the plug from the opening of the proximal end portion.

In some aspects of the present disclosure, anchoring the gastric tube may include inflating a balloon supported on the elongate tube with an inflation medium to wedge the balloon between inner surfaces of the stomach.

In embodiments, guiding the gastric tube along the enteral pathway may include advancing the gastric tube from an oral cavity through an esophagus and into an antrum of a stomach.

In some embodiments, the method may further include moving a movable component supported on the elongate tube from an unexpanded configuration to an expanded configuration in which the movable component bows outwardly from the outer surface of the elongate tube into engagement with a portion of the stomach. Moving the movable component may include sliding the movable component in a distal direction relative to the elongate tube.

In further embodiments of the present disclosure, the plug may include a tether attached to the outer surface of the elongate tube. The plug may include a plurality of stacked conical bodies.

Other aspects, features, and advantages of the present disclosure will be apparent from the description, the drawings, and the claims.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

As used herein, the term "clinician" refers to a doctor, nurse, or other care provider and may include support personnel. The terms "proximal" or "trailing" each refer to the portion of a structure closer to a clinician, and the terms "distal" or "leading" each refer to a portion of a structure farther from the clinician.

Figure 1:
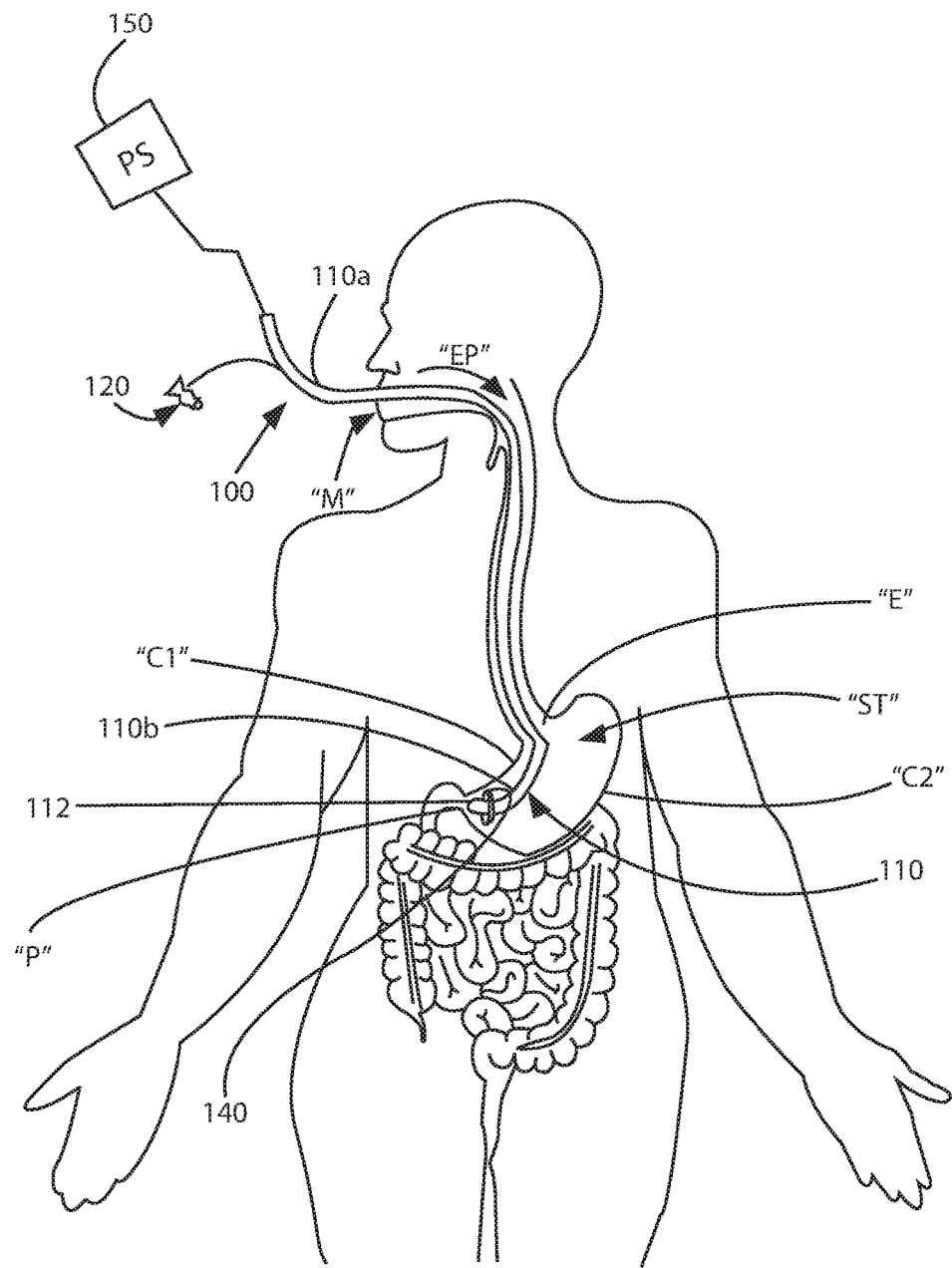
FIG. 1 is a side view of an illustrative embodiment of a gastric tube being navigated through an enteral pathway of a patient into a stomach of the patient in accordance with the principles of the present disclosure.
Figure 2:
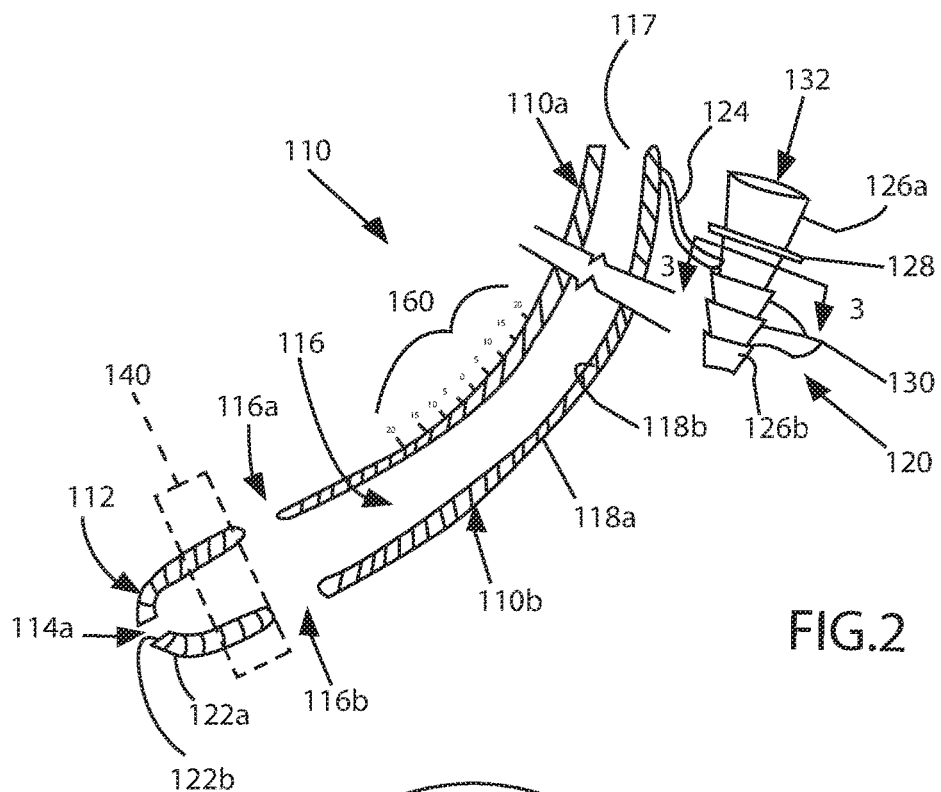
FIG. 2 is a side view, in part cross section and in part phantom, of the gastric tube shown in FIG. 1.
Figure 3:
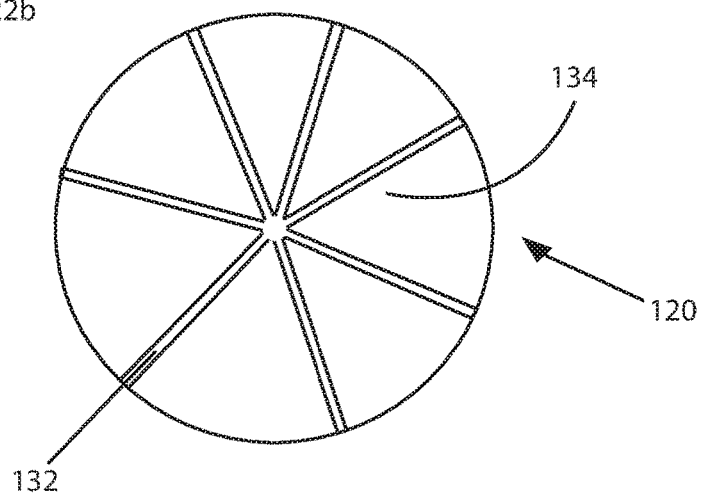
FIG. 3 is a cross section of the plug of the gastric tube taken along line 3-3 in FIG. 2.

Referring now to FIG. 1, a gastric tube 100 includes an elongate tube 110, a cannulated plug 120 coupled to the elongate tube 110 and configured for connection with a vacuum source 152 (FIG. 5), and an anchor, such as, for example, an inflatable balloon member 140 supported on the elongate tube 110.

In use, as described in further detail below with reference to FIGS. 5-7, the gastric tube 100 is inserted into an oral cavity (e.g., a mouth "M") of a patient and is advanced distally (e.g., caudally) along an enteral pathway "EP" that includes a track that extends between oral cavity "M" and a stomach "ST" of the patient. When positioned in the stomach "ST" of the patient (e.g., the antrum or lower part of the stomach), the balloon member 140 can be secured within or fixed to the stomach "ST" by, for example, inflating the balloon member 140 and aid the clinician in performing a bariatric surgical procedure such as a sleeve gastrectomy. Prior to and/or after inflating the balloon member 140, vacuum source 152 is connected to the plug 120 and activated to draw or aspirate fluids from the stomach "ST."

With reference to FIGS. 1-4, the elongate tube 110 can be formed of any material with sufficient flexibility to enable the elongate tube 110 to maneuver along the patient's track or enteral pathway "EP" between the oral cavity "M" and the stomach "ST." In embodiments, elongate tube 110 is fabricated from an elastomer, such as, for example, a silicone containing material. The elongate tube 110 includes a trailing end portion or proximal end portion 110a and a leading end portion or distal end portion 110b. Elongate tube 110 defines a curved length that extends between the proximal and distal end portions 110a, 110b. It is contemplated that elongate tube 110 can be linear, arcuate, or any shape suitable for a particular bariatric surgical procedure. Elongate tube 110 defines a lumen 116 extending along and through the length of elongate tube 110. The lumen 116 is in fluid communication with side openings 116a, 116b defined in an outer surface 118a of elongate tube 110 adjacent distal end portion 110b.

Proximal end portion 110a includes an opening 117 in communication with lumen 116. Opening 117 of proximal end portion 110a is configured for removable receipt of cannulated plug 120, as will be described in greater detail below. Distal end portion 110a includes a distal tip 112. Distal tip 112 has a blunt, arcuate outer surface 122a such that penetration of tissue during the advancement of elongate tube 110 through internal body cavities of a patient is resisted and/or prevented. In some embodiments, distal tip 112 can be variously configured, such as, for example, oval, oblong, tapered, uniform, non-uniform, smooth, polished, and/or rounded. Distal tip 112 further includes an arcuate inner surface 122b separated from outer surface 122a by a thickness of distal tip 112. Distal tip 112 defines a distal recess or opening 114a defined in a leading end of the distal tip 112 and extending between inner and outer surfaces 122a, 122b. The side openings 116a, 116b and distal opening 114a together function as an inlet that draws bodily fluids in when lumen 116 is coupled to a vacuum source 152 (FIG. 5). The vacuum source 152 couples to lumen 116 via plug 120 to aspirate bodily fluids out of a surgical site such as an antrum of a stomach.

Gastric tube 100 further includes cannulated plug 120 coupled to elongate tube 110. Plug 120 includes a tether 124 attached to outer surface 118a of elongate tube 110. Plug 124 tapers from a proximal end 126a to a distal end 126b thereof. Proximal end 126a is configured for detachable connection with vacuum source 152 such that a pressure differential can be generated within plug 120. Plug 120 includes a radial extension 128 disposed about proximal end 126a. Radial extension 128 has an outer diameter equal to a diameter of opening 117 of proximal end portion 110a (i.e., inner diameter of tube 110) such that radial extension 128 is frictionally engaged with an inner surface 118b of elongate tube 110 when plug 120 is received within opening 117. In this way, fluid and/or air is resisted and/or prevented from passing between radial extension 128 and inner surface 118b of elongate tube 110.

Distal end 126b of plug 120 is configured for removable receipt in opening 117 of proximal end portion 110a of elongate tube 110 to control flow of one of aspiration and irrigation through lumen 116 of elongate tube 110. Distal end 126b includes a plurality of stacked conical bodies 130 that increase the strength of the connection of plug 120 with elongate tube 110. Conical bodies 130 taper in a proximal-distal direction along plug 120.

Plug 120 defines a passageway 132 extending from proximal end 126a to distal end 126b. Passageway 132 includes a pressure valve 134 disposed therein. Pressure valve 134 is resiliently biased to a closed configuration in which pressure valve 134 resists and/or prevents fluid from passing through passageway 132. When a pressure differential generated by vacuum source 152 reaches a selected threshold value, the resilient bias of valve 134 is overcome such that valve 134 moves to an open position in which fluid is free to pass through passageway 132.

Figure 4:
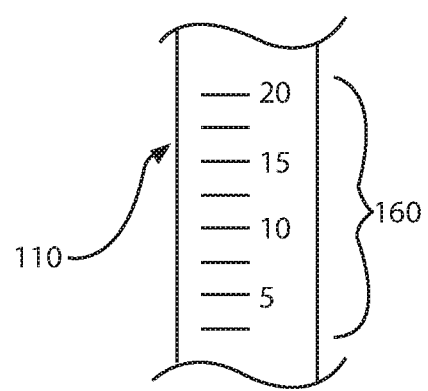
FIG. 4 is an expanded view of depth markings of the gastric tube shown in FIG. 1.

With reference to FIG. 4, the elongate tube 110 may include one or more depth markings 160 on outer surface 118a of elongate tube 110 that function as an indicator for an insertion depth of the gastric tube 100 along the enteral pathway "EP" of the patient.

Figures 5, 6:
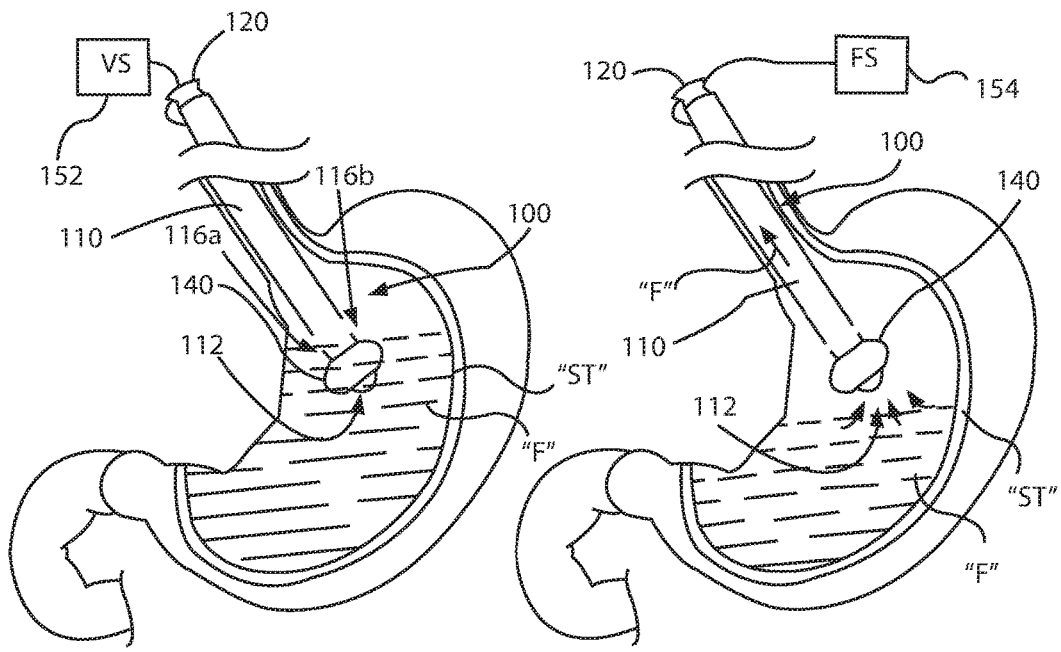
FIGS. 5 and 6 are progressive side views of the gastric tube shown in FIG. 1 aspirating bodily fluid from within a stomach.
Figure 7:
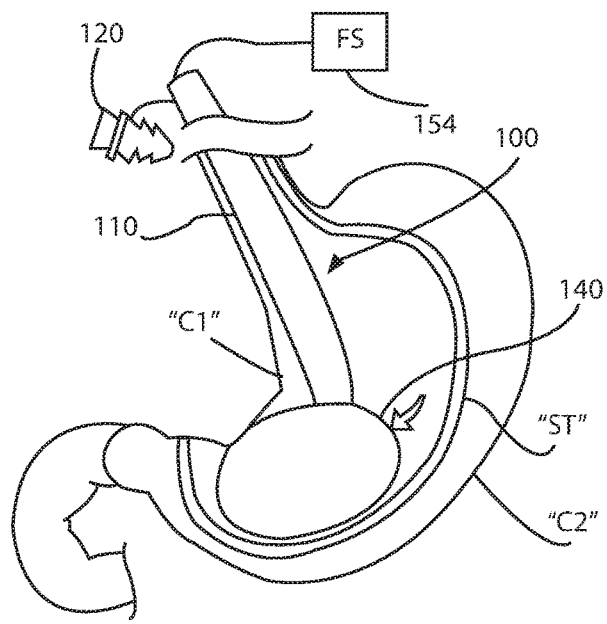
FIG. 7 is a side view of the gastric tube shown in FIG. 5 secured to a stomach.

With reference to FIGS. 5-7, gastric tube 100 may further include an anchor, such as, for example, an inflatable balloon member 140 secured to elongate tube 110. Balloon member 140 is configured to fix elongate tube 110 within a patient's stomach. Balloon member 140 can be in the form of a toroid that is disposed about outer surface 118a of distal end portion 110b such that distal tip 112 protrudes distally from balloon member 140. Balloon member 140 is positioned along outer surface 118a without blocking side openings 116a, 116b. It should be appreciated that, as used herein, the term inflatable balloon member refers to any structure defining a volume that is expandable upon introduction of fluid into the volume, and thus can include a unitary arrangement of material and/or a multi-component arrangement secured together to form, for example, a bladder.

An inflation lumen (not shown) is defined in the elongate tube 110 that is in fluid communication with balloon member 140. The balloon member 140 is adapted to receive inflation fluid (e.g., saline) through the inflation lumen when the inflation lumen is coupled to fluid source 154 adapted to deliver the inflation fluid. Alternatively, and/or additionally, the inflation lumen couples to vacuum source 152 adapted to create a vacuum in the inflation lumen to draw inflation fluid from within the balloon member 140 out of the balloon member 140 to deflate the balloon member 140. As appreciated, the fluid and/or vacuum sources 152, 154 enable a clinician to control the size of the balloon member 140 as desired.

In an exemplary use, as illustrated in FIGS. 5-7, the gastric tube 100 is inserted into a patient, such as, for example, an oral cavity "M" of a patient and is advanced distally toward the stomach "ST" along enteral pathway "EP," which extends from the oral cavity "M," through the esophagus "E," and into the stomach "ST." The gastric tube 100 is selectively repositioned based on observed positions of the distal tip 112 along the enteral pathway "EP." Gastric tube 100 is further guided through the esophagus "E" and selectively positioned within the stomach "ST" of the patient.

Upon positioning the gastric tube 100 within the stomach "ST," the vacuum source 152 functions to aspirate bodily fluid "F" in the stomach "ST." In particular, actuation of the vacuum source 152 creates a pressure differential that overcomes the resilient bias of valve 134 to move valve 134 from the closed position to the open position. With valve 134 in the open position, pressure is generated in the lumen 116 and draws the bodily fluid "F" into the distal opening 114a of the distal tip 112 and/or side openings 116a, 116b of elongate tube 110 for proximal extraction of the bodily fluid "F" through lumen 116, passageway 132 of plug 120 and out of proximal opening 117 of elongate tube 110. As can be appreciated, the vacuum source 152 can also function to collapse the stomach "ST" or portions thereof to facilitate any suitable bariatric procedure such as a sleeve gastrectomy.

When aspiration of bodily fluid "F" is completed, vacuum source 152 is deactivated such that valve 134 moves from the open position to the closed position in which fluid cannot leak in a distal direction through lumen 116 back into the stomach "ST." In some embodiments, alternatively to deactivating vacuum source 152, valve 134 or any type of suitable valve described herein can be manually closed to resist and/or prevent fluid from passing through passageway 132. Plug 120 may be removed from opening 117 of proximal end portion 110a while remaining connected to vacuum source 152 to free up opening 117 for connection to another device, such as, for example, a fluid source 154.

As shown in FIG. 7, the fluid source 154 couples to the gastric tube 100 to partially and/or wholly inflate the balloon 140 to anchor the gastric tube 100 within the selected position within the stomach "ST" (e.g., the antrum) and aid the clinician in performing the bariatric surgical procedure. In some embodiments, fluid source 154 is coupled to elongate tube 110 via plug 120. As the balloon member 140 is inflated with inflation medium, balloon member 140 is wedged between a first inner surface or a lesser curvature portion "C1" of stomach "ST" and a second inner surface or greater curvature portion "C2" of stomach "ST." With the balloon 140 deflated, a clinician can remove or transect a large portion of the stomach "ST" and staple the remaining portion together. In certain procedures, this is done to limit the size of the patient's stomach "ST" for helping the patient lose weight.

Figure 8:
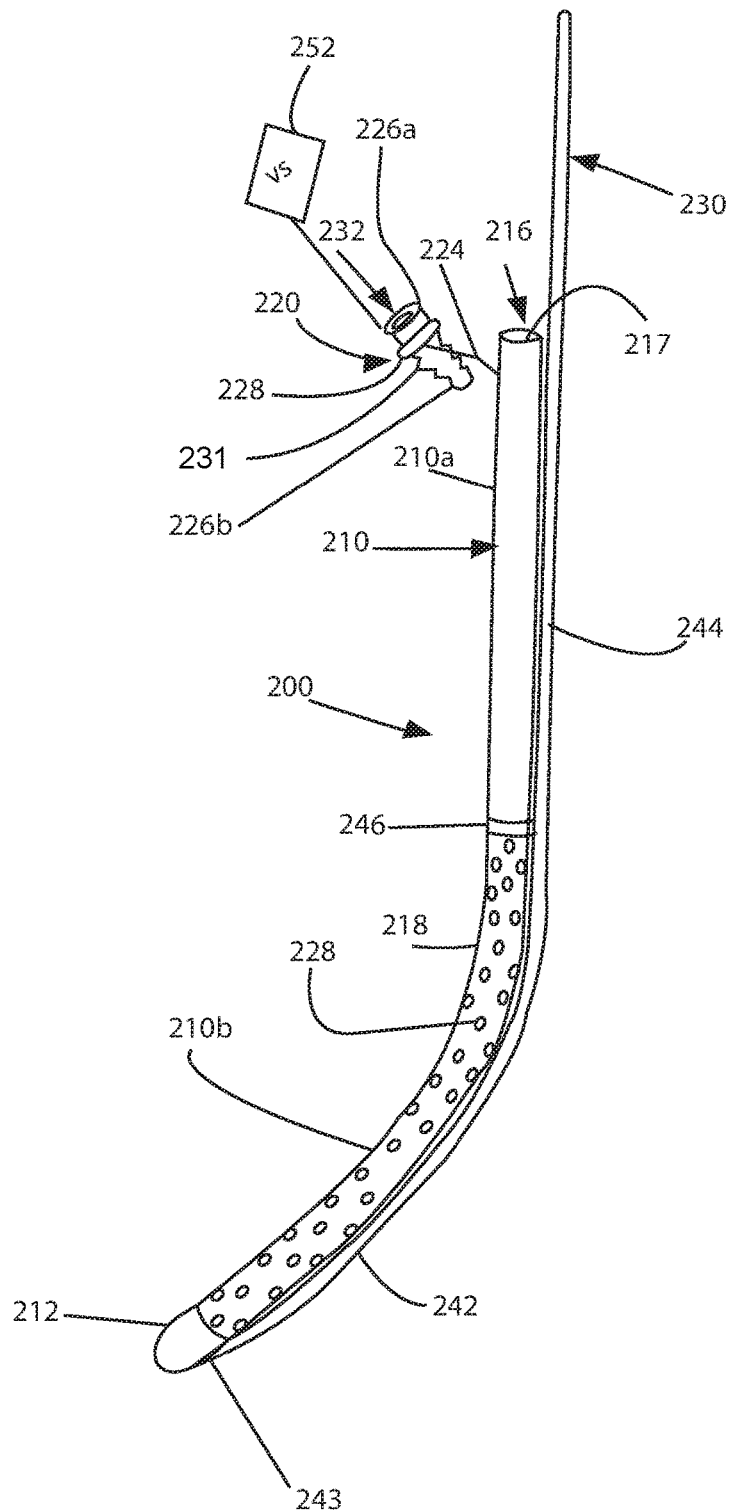
FIG. 8 is a perspective view of another illustrative embodiment of a gastric tube having a movable component disposed in an unexpanded position in accordance with the principles of the present disclosure.

Referring now to FIGS. 7 and 8, another embodiment of a gastric tube 200, similar to gastric tube 100 discussed above, is shown. In general, the gastric tube 200 includes an elongate tube 210 having a plurality of openings or apertures 228 and coupled to a cannulated plug 220, similar to plug 120 discussed above, configured for connection with a vacuum source 252, and a rod member or movable component 230 coupled to elongate tube 210. When suction is applied to elongate tube 210, elongate tube 210 can adhere to tissue, such as, for example, stomach tissue, due to the plurality of openings 228. In embodiments, the gastric tube 100 described with regard to FIGS. 1-7 may also include movable component 230 translatably or slidably coupled to elongate tube 110 thereof.

The elongate tube 210 includes a trailing end portion or proximal end portion 210a and a leading end portion or distal end portion 210b. Elongate tube 210 defines a curved length that extends between the proximal and distal end portions 210a, 210b. Elongate tube 210 defines a lumen 216 extending along and through the length of elongate tube 210. Elongate tube 210 further includes a plurality of openings or apertures 228 extending between an outer surface 218 and an inner surface (not shown) of elongate tube 210. Apertures 228 provide for fluid communication between lumen 216 and an environment exterior to elongate tube 210. Proximal end portion 210a includes an opening 217 configured for removable receipt of plug 220. Distal end portion 210b includes a distal tip 212, similar to distal tip 112 discussed above.

Gastric tube 200 further includes cannulated plug 220 coupled to elongate tube 210. Plug 220 includes a tether 224 attached to outer surface 218 of elongate tube 210. Plug 220 tapers from a proximal end 226a to a distal end 226b thereof. Proximal end 226a is configured for detachable connection with a vacuum source 252 such that a pressure differential can be generated within plug 220. Plug 220 includes a radial extension 228 disposed about proximal end 226a. Radial extension 228 has an outer diameter equal to a diameter of opening 217 of proximal end portion 210a (i.e., inner diameter of tube 210) such that radial extension 228 is frictionally engaged with the inner surface (not shown) of elongate tube 210 when plug 220 is received within opening 217. In this way, fluid and/or air is resisted and/or prevented from passing between radial extension 228 and the inner surface of elongate tube 210.

Distal end 226b of plug 220 is configured for removable receipt in opening 217 of proximal end portion 210a of elongate tube 210 to control flow of one of aspiration and irrigation through lumen 216 of elongate tube 210. Distal end 226b includes a plurality of stacked conical bodies 231 that increase the strength of the connection of plug 220 with elongate tube 210. Conical bodies 231 taper in a proximal-distal direction along plug 220.

Plug 220 defines a passageway 232 extending from proximal end 226a to distal end 226b. Passageway 232 includes a pressure valve (not shown), similar to pressure valve 134 discussed above, disposed therein. The pressure valve is resiliently biased to a closed configuration in which pressure valve resists and/or prevents fluid from passing through passageway 232. When a pressure differential generated by vacuum source 252 reaches a selected threshold value, the resilient bias of the pressure valve is overcome such that the pressure valve moves to an open position in which fluid is free to pass through passageway 232.

Gastric tube 200 includes a movable component 230 coupled to elongate tube 210. Movable component 230 is formed from a semi-rigid, resiliently flexible material, e.g., a suitable elastomer, and defines a length greater than the length of elongate tube 210 such that movable component 230 can be accessed outside the patient and/or remotely of the surgical site. Movable component 230 defines a distal portion 242 having a distal end 243 and a proximal portion 244. Distal end 243 of movable component 230 is integrally, i.e., monolithically, formed with or otherwise affixed to distal tip 212. A coupling 246, e.g., a ring, sleeve, hook, latch, etc., affixed to elongate tube 210 slidably receives a portion of movable component 230 therethrough to slidably couple movable component 230 to elongate tube 210 intermediate the distal and proximal end portions 210a, 210b of elongate tube 210.

Figure 9:
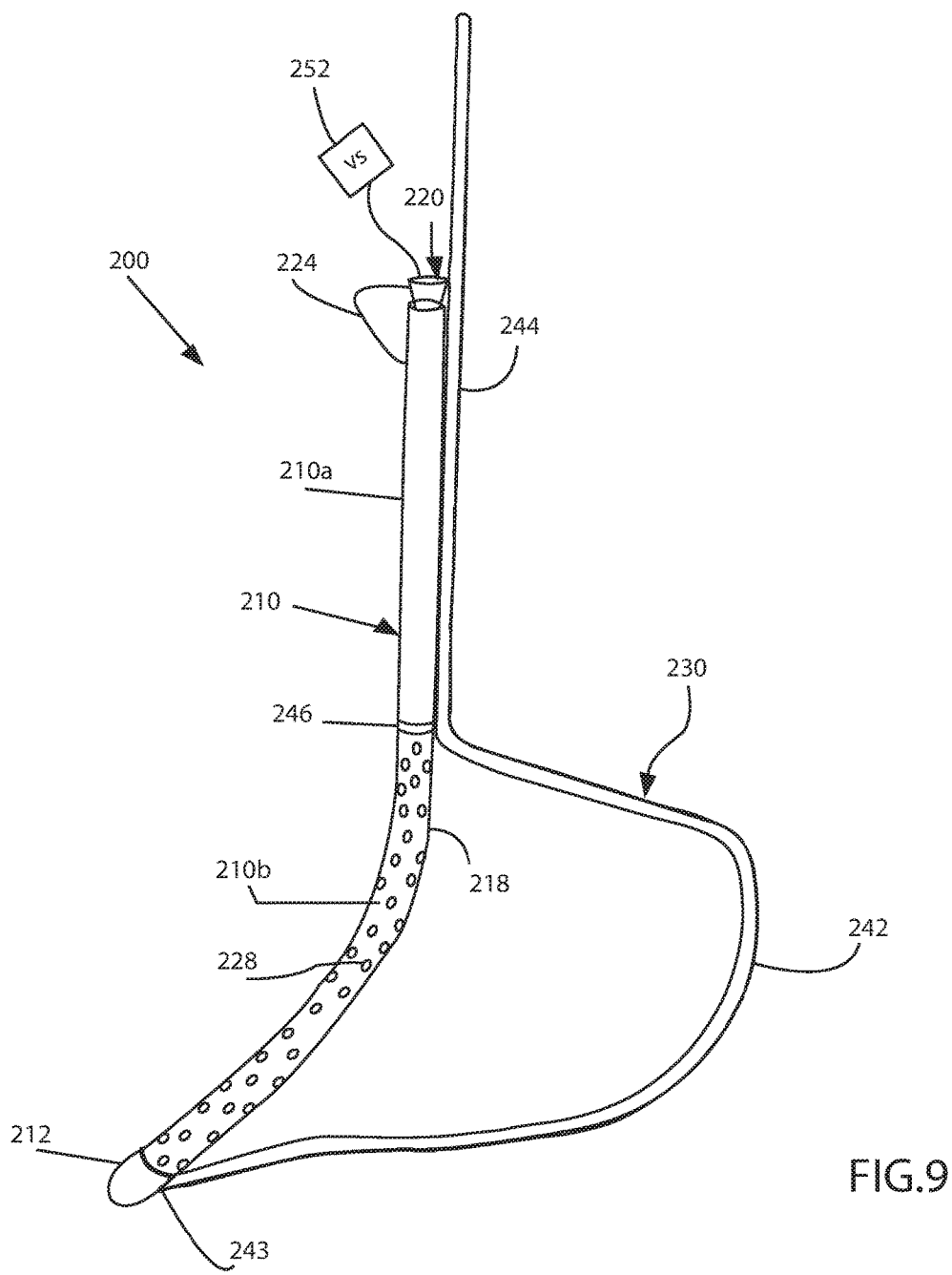
FIG. 9 is perspective view of the gastric tube shown in FIG. 7 with the movable component disposed in an expanded position.

As a result of the above-configuration, movable component 230 is slidable through coupling 246 and relative to elongate tube 210 between an unexpanded or contracted position and an expanded or deployed position. The unexpanded position corresponds to a first condition of gastric tube 200, as shown in FIG. 8, wherein distal portion 242 of movable component 230 extends along and is in abutting engagement with the outer surface 218 of elongate tube 210 and is in substantially parallel relation relative thereto. The expanded position corresponds to a second condition of gastric tube 200, as shown in FIG. 9, wherein distal portion 242 of movable component 230 is bowed outwardly from elongate tube 210 and is spaced therefrom. In the expanded position, movable component 230 defines a configuration that generally complements the curvature of a greater curvature portion of a stomach (FIG. 7).

Proximal portion 244 of movable component 230 may be grasped and manipulated relative to elongate tube 210 to transition movable component 230 between the unexpanded and expanded positions. As mentioned above, movable component 230 is dimensioned such that proximal portion 244 is accessible from outside the patient, thus readily enabling manipulation thereof. More specifically, translating movable component 230 distally relative to elongate tube 210 and coupling 246 urges movable component 230 distally through coupling 246 such that distal portion 242 of movable component 230 is bowed outwardly relative to elongate tube 210 towards the expanded position. Translating movable component 230 proximally relative to elongate tube 210 pulls movable component 230 proximally through coupling 246 such the distal portion 242 of movable component 230 is pulled inwardly relative to elongate tube 210 towards the unexpanded position.

In an exemplary use, with movable component 230 in the unexpanded position, the gastric tube 200 is inserted into a patient, such as, for example, an oral cavity of a patient and is distally advanced toward a stomach of the patient along an enteral pathway that extends from the oral cavity, through an esophagus of the patient, and into the stomach, as described above with regard to FIGS. 1-7. Gastric tube 200 is guided along the enteral pathway via observation of the distal tip 212. The gastric tube 200 is selectively repositioned based on observed positions of the distal tip 212 along the enteral pathway. Gastric tube 200 is further guided through the esophagus and selectively positioned within the stomach of the patient.

Upon positioning the gastric tube 200 within the stomach, proximal portion 244 of movable component 230 is translated distally relative to elongate tube 210 such that distal portion 242 of movable component 230 bows outwardly relative to elongate tube 210 towards the expanded position. As distal portion 242 of movable component 230 bows outwardly towards the expanded position, elongate tube 210 is urged towards and into complementary mating relation with the lesser curvature portion of the stomach, while distal portion 242 of movable component 230 is urged towards and into complementary mating relation with the greater curvature portion of the stomach. As such, the orientation of gastric tube 200 with elongate tube 210 extending along the lesser curvature portion of the stomach between the esophageal sphincter and the pyloric sphincter can be readily achieved. As a result of this configuration of gastric tube 200 in the expanded position, the above-described orientation of gastric tube 200 within the stomach is maintained despite spasms, folding, spiraling, and/or shifting of the stomach.

Once the proper orientation of elongate tube 210 has been achieved, suction is applied within lumen 216 for suctioning any remaining contents within the stomach into lumen 216 of elongate tube 210 through apertures 228. In particular, actuation of the vacuum source 252 creates a pressure differential that overcomes the resilient bias of the pressure valve to move valve from the closed position to the open position. With the pressure valve in the open position, pressure is generated in lumen 216 and draws the bodily fluid from the stomach into the apertures 228 of elongate tube 210 for proximal extraction of the bodily fluid through lumen 216, passageway 232 of plug 220 and out of proximal opening 217 of elongate tube 210.

Application of suction within lumen 216 also suctions the lesser curvature portion of the stomach to the outer surface or periphery 218 of elongate tube 210, to ensure and maintain the complementary mating relation of elongate tube 210 with the lesser curvature portion of the stomach.

With elongate tube 210 maintained in position relative to the lesser curvature portion of the stomach as a result of the applied suction, proximal portion 244 of movable component 230 is translated proximally relative to elongate tube 210 such that the distal portion 242 of movable component 230 is pulled inwardly relative to elongate tube 210 back to the unexpanded position. As suction is maintained at this point, elongate tube 210 is maintained in the position detailed above despite contraction of distal portion 242 of movable component 230.

Once distal portion 242 of movable component 230 has been returned to the unexpanded position, transection of the stomach adjacent elongate tube 210 on an opposite side of elongate tube 210 relative to the lesser curvature portion of the stomach may be effected in any suitable fashion, e.g., using a stapling device or other suitable device. Transection in this manner reforms the stomach to a tubular-shaped configuration that generally approximates the outer dimension of elongate tube 210 and extends between the esophageal sphincter and the pyloric sphincter. As can be appreciated, the diameter of elongate tube 210 may be selected in accordance with a desired diameter of the tubular-shape reformed stomach.

When transaction is completed, vacuum source 252 is deactivated such that the pressure valve moves from the open position to the closed position in which fluid cannot leak in a distal direction through lumen 216 back into the stomach. Plug 220 may be removed from opening 217 of proximal end portion 210a while remaining connected to vacuum source 252 to free up opening 217 for connection to another device, such as, for example, a fluid source.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described herein, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A gastric tube for use in a bariatric procedure, the gastric tube comprising:
    an elongate tube having a proximal end portion and a distal end portion, the elongate tube defining a lumen along a length thereof, the proximal end portion defining an opening in communication with the lumen, the elongate tube including:
        a blunt tip formed on the distal end portion; and
        an outer surface that extends between the proximal and distal end portions and defines a side opening in communication with the lumen, the side opening configured and dimensioned for at least one of aspiration or irrigation; and
    a cannulated plug coupled to the elongate tube, the cannulated plug including:
        a valve resiliently biased towards a closed position;
        a proximal end configured for connection to a vacuum source; and
        a distal end configured for removable receipt in the opening of the proximal end portion of the elongate tube to control a flow of one of aspiration or irrigation through the lumen.

2. The gastric tube as recited in claim 1, wherein the cannulated plug includes a tether attached to the outer surface of the elongate tube.

3. The gastric tube as recited in claim 1, wherein the cannulated plug includes a radial extension and the elongate tube includes an inner surface, wherein the radial extension has an outer diameter equal to a diameter of the opening of the proximal end portion such that the radial extension is frictionally engaged with the inner surface of the elongate tube when the cannulated plug is received in the opening.

4. The gastric tube as recited in claim 1, wherein the cannulated plug tapers between the proximal end and the distal end thereof.

5. The gastric tube as recited in claim 4, wherein the distal end of the cannulated plug includes a plurality of stacked conical bodies.

6. The gastric tube as recited in claim 1, wherein the elongate tube is pliable.

7. The gastric tube as recited in claim 1, further including a plurality of depth markings formed along at least a portion of the outer surface of the elongate tube.

8. The gastric tube as recited in claim 1, further including a movable component attached to the outer surface of the elongate tube, the movable component including a distal portion, the movable component being movable between an unexpanded position in which the movable component is disposed in abutting engagement with the outer surface of the elongate tube and an expanded position in which the distal portion of the movable component bows outwardly from the outer surface of the elongate tube.

9. The gastric tube as recited in claim 8, wherein the movable component is slidably coupled to the proximal end portion of the elongate tube and fixedly coupled to the distal end portion of the elongate tube.

10. A gastric tube for use in a bariatric procedure, the gastric tube comprising:
    an elongate tube having a proximal end portion and a distal end portion, the elongate tube defining a lumen along a length thereof, the proximal end portion defining an opening in communication with the lumen, the elongate tube including:
        a blunt tip formed on the distal end portion; and
        an outer surface that extends between the proximal and distal end portions and defines a side opening in communication with the lumen, the side opening configured and dimensioned for at least one of aspiration or irrigation; and
    a cannulated plug coupled to the elongate tube, the cannulated plug including:
        a proximal end configured for connection to a vacuum source; and a distal end configured for removable receipt in the opening of the proximal end portion of the elongate tube to control a flow of one of aspiration or irrigation through the lumen, wherein the distal end of the cannulated plug includes a plurality of stacked conical bodies.

11. The gastric tube as recited in claim 10, wherein the cannulated plug includes a valve resiliently biased towards a closed position.

12. The gastric tube as recited in claim 10, wherein the cannulated plug includes a tether attached to the outer surface of the elongate tube.

13. The gastric tube as recited in claim 10, wherein the cannulated plug includes a radial extension and the elongate tube includes an inner surface, wherein the radial extension has an outer diameter equal to a diameter of the opening of the proximal end portion such that the radial extension is frictionally engaged with the inner surface of the elongate tube when the cannulated plug is received in the opening.

14. The gastric tube as recited in claim 10, wherein the cannulated plug tapers between the proximal end and the distal end thereof.

15. The gastric tube as recited in claim 10, further including a plurality of depth markings formed along at least a portion of the outer surface.

16. The gastric tube as recited in claim 10, further including a movable component attached to the outer surface of the elongate tube, the movable component including a distal portion, the movable component being movable between an unexpanded position in which the movable component is disposed in abutting engagement with the outer surface of the elongate tube and an expanded position in which the distal portion of the movable component bows outwardly from the outer surface of the elongate tube.

17. The gastric tube as recited in claim 16, wherein the movable component is slidably coupled to the proximal end portion of the elongate tube and fixedly coupled to the distal end portion of the elongate tube.

18. A method of performing bariatric surgery, comprising:
inserting a gastric tube into an oral cavity of a patient, the gastric tube including:
an elongate tube having a proximal end portion and a distal end portion, the elongate tube defining a lumen along a length thereof, the proximal end portion defining an opening in communication with the lumen, the elongate tube including:
a blunt tip formed on the distal end portion; and
an outer surface that extends between the proximal and distal end portions and defines a side opening in communication with the lumen, the side opening configured and dimensioned for at least one of aspiration or irrigation; and
a cannulated plug coupled to the elongate tube, the cannulated plug including:
a proximal end configured for connection to a vacuum source; and
a distal end configured for removable receipt in the opening of the proximal end portion of the elongate tube to control a flow of one of aspiration or irrigation through the lumen;
guiding the gastric tube along an enteral pathway;
repositioning the gastric tube based on an observed position of the blunt tip to a selected position within a stomach of the patient;
aspirating fluid from the stomach through the side opening of the elongate tube;
removing the cannulated plug from the opening of the proximal end portion;
anchoring the gastric tube to the selected position; and
transecting a portion of the stomach.

19. The method of performing bariatric surgery as recited in claim 18, further including moving a movable component supported on the elongate tube from an unexpanded configuration to an expanded configuration in which the movable component bows outwardly from the outer surface of the elongate tube into engagement with a portion of the stomach.

20. The method of performing bariatric surgery as recited in claim 19, wherein moving the movable component includes sliding the movable component in a distal direction relative to the elongate tube.

* * * * *